(12) United States Patent
Kim et al.

(10) Patent No.: US 9,207,153 B2
(45) Date of Patent: Dec. 8, 2015

(54) TEST JIG

(71) Applicant: LG CHEM, LTD., Seoul (KR)

(72) Inventors: Heung Min Kim, Daejeon (KR); Han Sik Kim, Daejeon (KR); Seang Hee Chae, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 14/519,857

(22) Filed: Oct. 21, 2014

(65) Prior Publication Data

US 2015/0090048 A1    Apr. 2, 2015

Related U.S. Application Data

(63) Continuation of application No. PCT/KR2014/005019, filed on Jun. 5, 2014.

(30) Foreign Application Priority Data

Sep. 30, 2013  (KR) .................. 10-2013-0116299

(51) Int. Cl.
*G01N 3/02* (2006.01)
*G01N 3/04* (2006.01)
*G01N 3/08* (2006.01)
*G01N 19/08* (2006.01)
*G01R 1/04* (2006.01)

(52) U.S. Cl.
CPC .. *G01N 3/04* (2013.01); *G01N 3/08* (2013.01); *G01N 19/08* (2013.01); *G01R 1/0408* (2013.01); *G01N 2203/0296* (2013.01)

(58) Field of Classification Search
CPC .. G01R 1/0408; G01R 1/0466; G01R 1/0483; G01R 1/07314; G01R 31/26

USPC ............................................. 73/760, 856, 860
See application file for complete search history.

(56) References Cited

U.S. PATENT DOCUMENTS

| 2002/0017240 A1* | 2/2002 | Obana et al. ............... 118/712 |
| 2004/0020765 A1* | 2/2004 | Tanaka et al. ............. 204/280 |

(Continued)

FOREIGN PATENT DOCUMENTS

| EP | 1 394 874 A1 | 3/2004 |
| EP | 1 770 801 A1 | 4/2007 |

(Continued)

OTHER PUBLICATIONS

International Search Report, issued in PCT/KR2014/005019, mailed Sep. 18, 2014.

(Continued)

*Primary Examiner* — Max Noori
(74) *Attorney, Agent, or Firm* — Birch, Stewart, Kolasch & Birch, LLP

(57) ABSTRACT

Provided is a test jig including a jig main body having, at an end portion thereof, an insertion part into which an electrode lead is inserted and a fixing member detachably coupled to the insertion part to fix the electrode lead inserted to the insertion part, wherein the insertion part includes insertion faces outwardly extending from both end portions of the jig main body, and coupling faces extending from the insertion faces toward insides of the jig main body and brought into contact with the fixing member, and thus a tensile test is performed on an ultrasonic-welded portion of the electrode lead without an additional cell.

6 Claims, 7 Drawing Sheets

(56) References Cited

U.S. PATENT DOCUMENTS

| | | | |
|---|---|---|---|
| 2004/0070060 A1* | 4/2004 | Mamitsu et al. | 257/680 |
| 2005/0151550 A1* | 7/2005 | Lee et al. | 324/757 |
| 2008/0054921 A1* | 3/2008 | Kimura et al. | 324/754 |
| 2010/0099021 A1* | 4/2010 | Oikawa | 429/129 |
| 2013/0106453 A1* | 5/2013 | Ikegami | 324/750.19 |
| 2014/0203829 A1* | 7/2014 | Yamada | 324/750.08 |

FOREIGN PATENT DOCUMENTS

| | | |
|---|---|---|
| JP | 60-64272 U | 5/1985 |
| JP | 2011-100643 A | 5/2011 |
| JP | 2003-331816 A | 11/2013 |
| KR | 2001-0104454 A | 11/2001 |
| KR | 2001-0109588 A | 12/2001 |
| KR | 10-2008-0068305 A | 7/2008 |
| KR | 10-2012-0088120 A | 8/2012 |
| KR | 10-1242096 B1 | 3/2013 |
| KR | 10-2013-0065465 A | 6/2013 |

OTHER PUBLICATIONS

Written Opinion of the International Searching Authority, issued in PCT/KR2014/005019, mailed Sep. 18, 2014.
Supplementary European Search Report in EP 14783759.5 dated Jul. 29, 2015.

* cited by examiner

TEST JIG

CROSS-REFERENCE TO RELATED APPLICATIONS

This application is a Continuation of PCT International Application No. PCT/KR2014/005019 filed on Jun. 5, 2014, which claims priority under 35 U.S.C. 119(a) to Korean Patent Application No. 10-2013-0116299 filed in the Republic of Korea on Sep. 30, 2013, all of which are hereby expressly incorporated by reference into the present application.

BACKGROUND OF THE INVENTION

1. Field of the Invention

The present invention relates to a test jig, and more particularly, to a test jig implementing a tensile test for an ultrasonic-welded portion only using an electrode lead without use of a cell.

2. Description of the Related Art

In general, a secondary battery is used in the form of a unit cell and a plurality of unit cells are electrically connected to be used in a form of a battery module. For instance, small-sized devices such as mobile phones may work for a predetermined time with the output and capacity of a unit cell, whereas medium- or large-sized devices such as laptop computers, portable DVDs, small personal computers (PCs), electric vehicles, and hybrid vehicles require a battery module consisting of a plurality of unit cells due to limitations in their outputs and capacities.

The secondary battery is manufactured through a cell assembling process and a battery activation process. In the battery activation process, a cell is mounted on a predetermined jig for a smooth flow of electric current and conditions required for activation, or a tensile test is performed on an ultrasonic-welded portion of an electrode lead of the cell.

Meanwhile, since ultrasonic welding is performed for multiply connecting between a bus bar of the secondary battery and an electrode lead of the cell, the tensile test is performed on the ultrasonic-welded portion, wherein a destructive inspection is performed to measure a tensile force due to the nature of the welding.

Specifically, the tensile test is performed on the ultrasonic-welded portion, as illustrated in FIGS. 1 and 2, in a state where upper and lower jigs 20 and 30 are coupled to an upper part and a lower part of a cell 10 provided with an electrode lead 11, respectively.

However, the secondary battery according to the related art can not reuse the cell provided with the electrode lead 11, which has been subjected to the tensile test, thereby remarkably increasing unnecessary cost.

SUMMARY OF THE INVENTION

An aspect of the present invention provides a test jig which is shaped like a cell and repeatedly usable to perform a tensile test on an ultrasonic-welded portion of an electrode lead, so as to minimize waste of expenses and enhance work efficiency.

According to an aspect of the present invention, there is provided a test jig including a jig main body having, at an end portion thereof, an insertion part into which an electrode lead is inserted and a fixing member detachably coupled to the insertion part to fix the electrode lead inserted to the insertion part, wherein the insertion part comprises insertion faces outwardly extending from both end portions of the jig main body, and coupling faces extending from the insertion faces toward insides of the jig main body and brought into contact with the fixing member.

Meanwhile, the insertion face is inclined outwardly.

A guide protrusion is provided on a side portion of the fixing member, and a guide groove is provided in a sidewall of the insertion part to allow the guide protrusion to be slidably coupled thereto.

Pads having a buffering force are provided on corresponding portions of the insertion part and the fixing member which face each other.

An indicating part indicating a center of the insertion face is provided on the insertion face, so as to place the electrode lead at the center of the insertion face.

A latch part for latching a rear end of the electrode lead is provided on the insertion face, and the latch part is inserted into a latch groove provided in the bottom surface of the fixing member during coupling of the fixing member.

BRIEF DESCRIPTION OF THE DRAWINGS

The above and other aspects, features and other advantages of the present invention will be more clearly understood from the following detailed description taken in conjunction with the accompanying drawings, in which.

DETAILED DESCRIPTION OF THE PREFERRED EMBODIMENT

Figure 1:
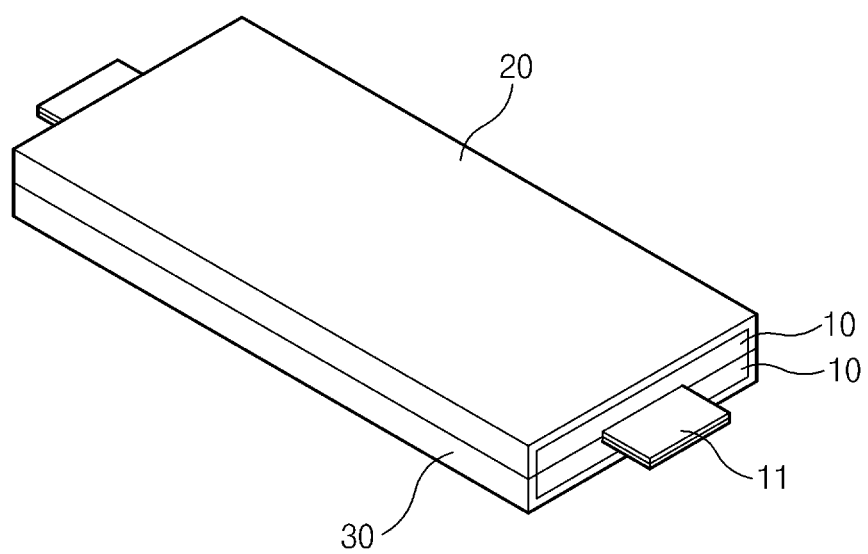
FIG. 1 is an exploded perspective view illustrating a tensile test jig according to a related art.
Figure 2:
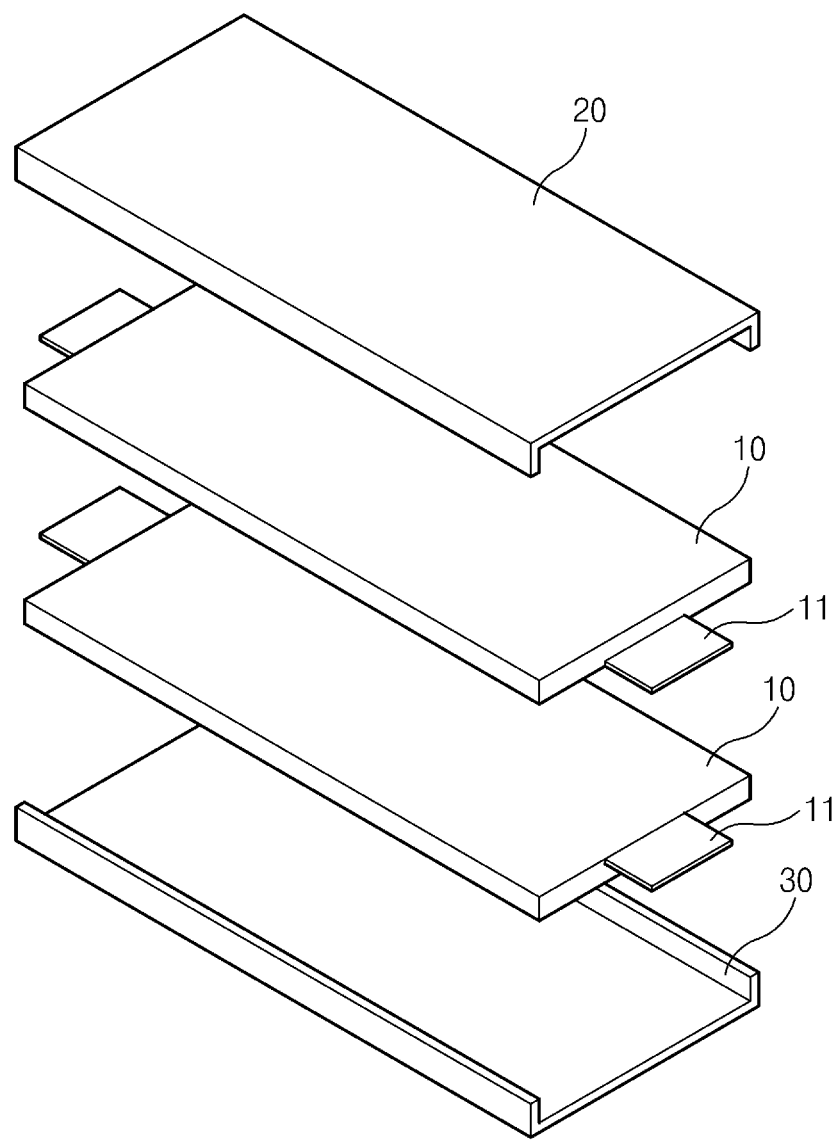
FIG. 2 is an assembled perspective view illustrating the tensile test jig according to the related art.

Exemplary embodiments of the present invention will now be described in detail with reference to the accompanying drawings.

In a test jig according to the present invention, electrode leads are fixedly inserted into both ends of the test jig, which makes it possible to perform a tensile test on an ultrasonic-welded portion of the electrode lead without using an additional cell, thereby reducing costs and enhancing work efficiency.

Hereinafter, with reference to the accompanying drawings, embodiments of the present invention will be described in detail enough for those of ordinary skilled in the art to easily perform embodiments of the invention. The invention may, however, be embodied in many different forms and should not be construed as being limited to the embodiments set forth herein. In the following description of the present invention, a detailed description of known functions and configurations incorporated herein will be omitted to avoid making the subject matter of the present invention unclear and, in every possible case, like reference numerals are used for referring to the same or similar elements in the description and drawings.

Figure 3:
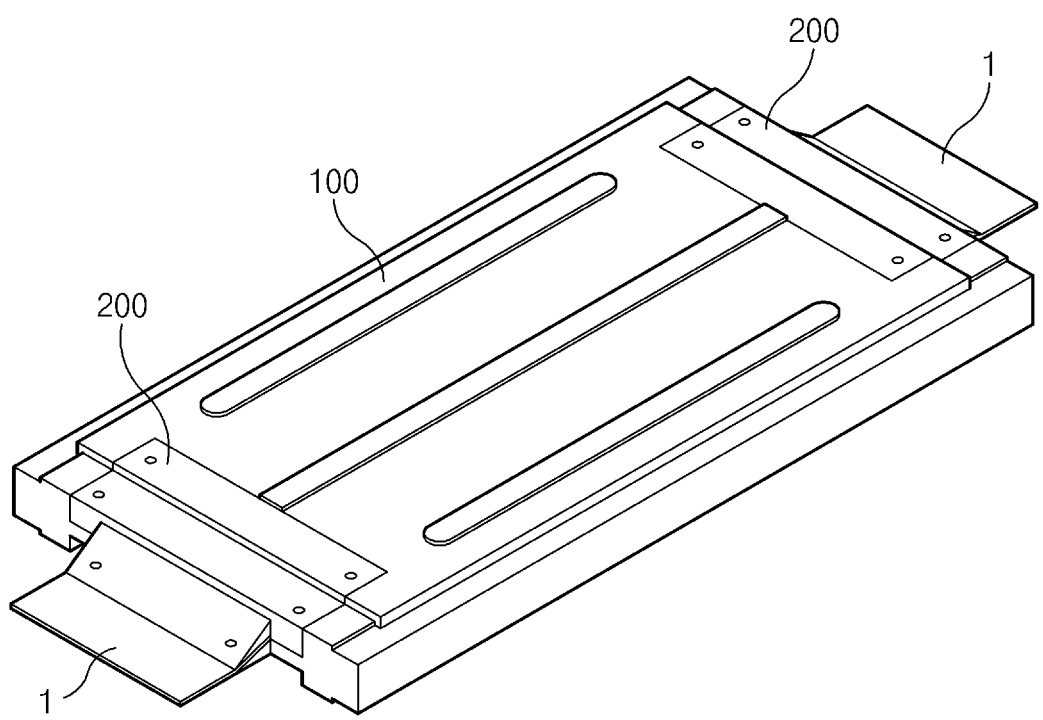
FIG. 3 is a perspective view illustrating a test jig according to a first embodiment of the present invention.
Figure 4:
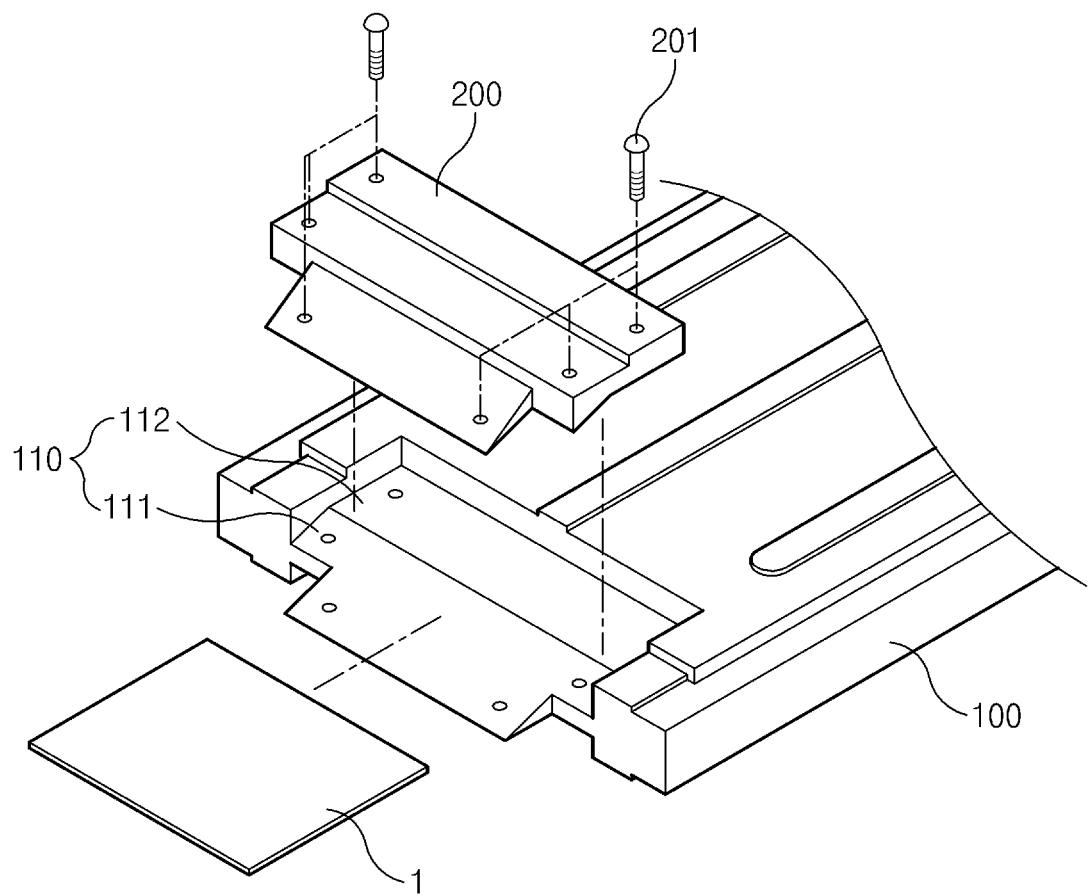
FIG. 4 is a partial enlarged perspective view illustrating the test jig according to the first embodiment of the present invention.

According to a first embodiment of the present invention, as illustrated in FIGS. 3 and 4, a test jig into which electrode leads are fixedly inserted includes a jig main body 100 into which electrode leads 1 are inserted, and a fixing member 200 fixing the electrode leads 1 inserted into the jig main body 100.

The jig main body 100 is shaped like a cell, and includes insertion parts 110 into which the electrode leads 1 are inserted at both ends thereof, wherein the insertion parts 110 includes insertion faces 111 outwardly extending from the both end portions of the jig main body 100 and supporting the electrode leads 1, and coupling faces 112 extending from the insertion faces 111 toward insides of the jig main body 100 and brought into contact with the fixing member 200 which will be described later.

As the jig main body 100 is manufactured in the shape of a cell to play a role of the cell, an additional cell is not needed. In other words, it is possible to perform a tensile test on the ultrasonic-welded portion in a state where the electrode leads 1 are inserted into the insertion parts 110 of the jig main body 100.

The jig main body 100 herein may be manufactured in various shapes in accordance with the size and shape of a cell applied to a battery.

Meanwhile, the insertion face 111 is inclined outwardly, and accordingly the electrode lead 1 is slantly placed to increase work efficiency for the tensile test.

The fixing member 200, which is provided for fixing the electrode lead 1 inserted into the insertion part 110, is brought into contact with the insertion part 110 and fixed to the jig main body 100 by using a plurality of bolts 201 as a fixing means.

According to the first embodiment of the present invention, the test jig 100 inserts the electrode lead 1 into the insertion face 111 of the insertion part 110 provided in the jig main body 100, and then brings the fixing member 200 into contact with the insertion part 110. Next, the fixing member 200 is fixed to the jig main body by using the plurality of blots 201 to complete assembly, and then the tensile test is performed on the electrode lead 1 using the assembled test jig.

Therefore, the test jig according to the first embodiment of the present invention does not need to use the additional cell by virtue of the jig main body 100 manufactured in the shape of the cell.

Hereinafter, for convenience of explanation, descriptions for the same or similar configurations or features as those described in the foregoing embodiment shall be skipped.

Figure 5:
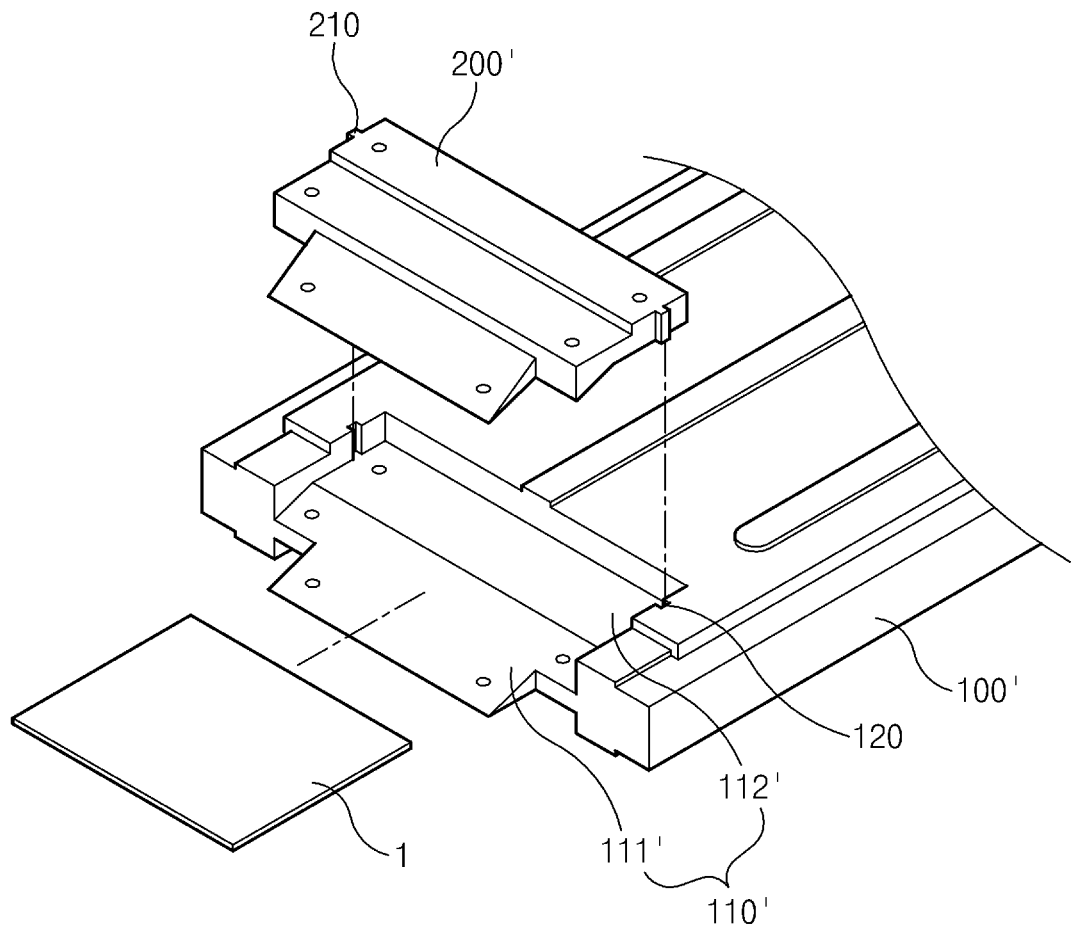
FIG. 5 is a perspective view illustrating a test jig according to a second embodiment of the present invention.

FIG. 5 is a perspective view illustrating a test jig according to a second embodiment of the present invention.

According to the second embodiment of the present invention, the test jig is configured such that a fixing member 200' is slidably coupled to an insertion part 110' by forming a guide protrusion and a guide groove on side portions of the insertion part 110' of the jig main body 100' and the fixing member 200', respectively.

That is, as illustrated in FIG. 5, the guide protrusion 210 is provided on the side portion of the fixing member 200' and the guide groove 120 is provided in the sidewall of the insertion part 110' to which the guide protrusion 210 is slidably coupled.

Therefore, when the jig main body 100' and the fixing member 200' are coupled, the test jig according to the second embodiment of the present invention may efficiently adjust bolt coupling holes to thereby enhance work efficiency and reduce the mobility of the fixing member 200' to increase a fixing force.

Figure 6:
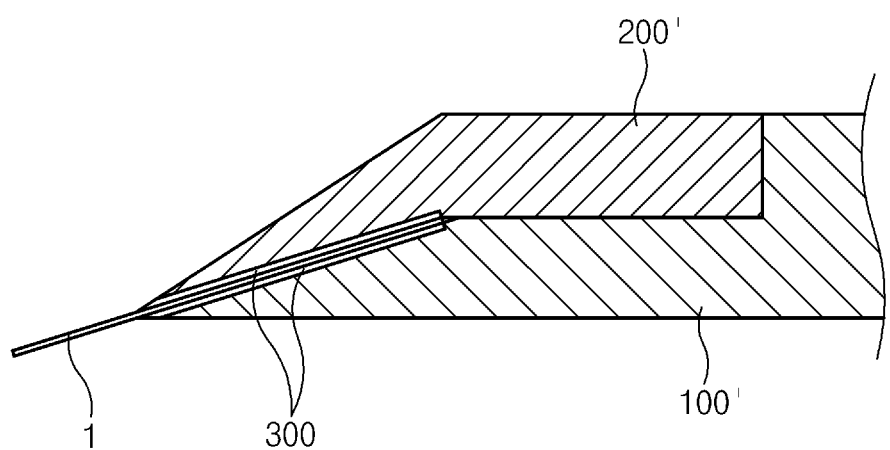
FIG. 6 is a cross sectional view of the FIG. 5.

Meanwhile, buffer parts 300 are further provided on corresponding portions of the insertion part 110' of the jig main body 100' and the fixing member 200' which face each other, as illustrated in FIG. 6. The buffer part 300 is supported by a surface of the electrode lead 1 to provide a pressing force more uniformly over an entire surface of the electrode lead 1 when coupling the fixing member 200' to the jig main body 100', thereby increasing a fixing force and also preventing the electrode lead 1 from being damaged and from having a tensile force due to the pressing force.

Figure 7:
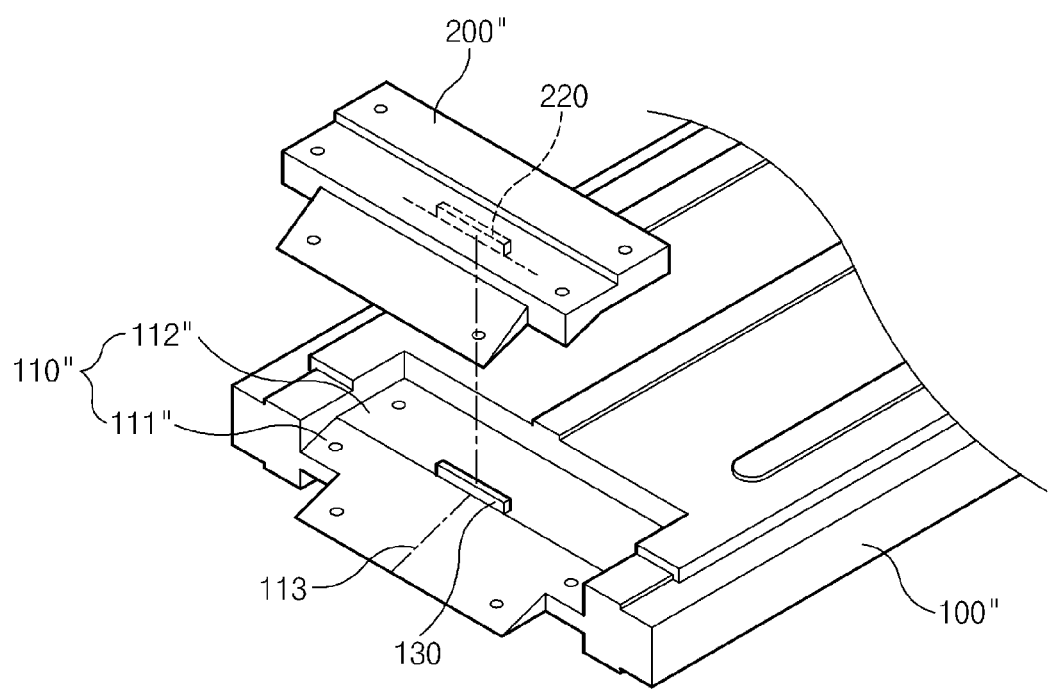
FIG. 7 is a perspective view illustrating a test jig according to a third embodiment of the present invention.

FIG. 7 is a perspective view illustrating a test jig according to a third embodiment of the present invention.

The test jig according to the third embodiment of the present invention, as illustrated in FIG. 7, includes a latch part 130 disposed at an interface between an insertion face 111" and a coupling face 112" of an insertion part 110" provided on a jig main body 100". The latch part 130 may uniformly adjust the heights of the electrode leads 1 by allowing end portions of the electrode leads 1 inserted to the insertion faces 111" to be latched and thus equally adjust withdrawal lengths of the electrode leads 1 inserted to a plurality of test jigs.

A latch groove 220 into which the latch part 130 is inserted is provided in a bottom surface of the fixing member 200" and a coupling force is increased by inserting the latch part 130 into the latch groove 220 to bring the fixing member 200" into contact with the insertion part 110.

An indicating part 113 is provided at the center of the insertion face 111" of the insertion part 110" in a longitudinal direction of the jig main body 100" and thus the electrode lead 1 may be adjusted to be positioned at the center of the insertion face 111", thereby equally adjusting left and right sides of the electrode leads 1 inserted into the plurality of test jigs.

According to the present invention, a tensile test is performed on an ultrasonic-welded portion of an electrode lead without use of an additional cell, thereby minimizing waste of unnecessary costs and enhancing work efficiency.

While the present invention has been shown and described in connection with the exemplary embodiments, it will be apparent to those skilled in the art that modifications and variations can be made without departing from the spirit and scope of the invention as defined by the appended claims.

What is claimed is:

1. A test jig comprising:
a jig main body having, at an end portion thereof, an insertion part into which an electrode lead is inserted; and
a fixing member detachably coupled to the insertion part to fix the electrode lead inserted to the insertion part,
wherein the insertion part comprises insertion faces outwardly extending from both end portions of the jig main body, and coupling faces extending from the insertion faces toward insides of the jig main body and brought into contact with the fixing member.

2. The test jig of claim 1, wherein the insertion face is inclined outwardly.

3. The test jig of claim 1, wherein a guide protrusion is provided on a side portion of the fixing member, and a guide groove is provided in a sidewall of the insertion part to allow the guide protrusion to be slidably coupled thereto.

4. The test jig of claim 1, wherein pads having a buffering force are provided on corresponding portions of the insertion part and the fixing member which face each other.

5. The test jig of claim 1, wherein an indicating part indicating a center of the insertion face is provided on the insertion face, so as to place the electrode lead at the center of the insertion face.

6. The test jig of claim 1, wherein a latch part for latching a rear end of the electrode lead is provided on the insertion face, and the latch part is inserted into a latch groove provided in the bottom surface of the fixing member during coupling of the fixing member.

* * * * *